(12) United States Patent
Alpern et al.

(10) Patent No.: US 8,594,408 B2
(45) Date of Patent: Nov. 26, 2013

(54) SYSTEMS AND METHODS FOR ANALYZING DYNAMIC DENTAL OCCLUSIONS AND MAKING DENTAL APPLIANCES

(75) Inventors: Michael C. Alpern, Port Charlotte, FL (US); Douglas G. Nuelle, Blue Ridge, GA (US)

(73) Assignee: Poly Virtual Occlusion, LLC, Punta Gorda, FL (US)

( * ) Notice: Subject to any disclaimer, the term of this patent is extended or adjusted under 35 U.S.C. 154(b) by 0 days.

(21) Appl. No.: 13/448,996

(22) Filed: Apr. 17, 2012

(65) Prior Publication Data
US 2013/0275107 A1   Oct. 17, 2013

(51) Int. Cl.
*G06K 9/00*       (2006.01)
*A61C 3/00*       (2006.01)

(52) U.S. Cl.
USPC .............................. 382/131; 382/154; 433/24

(58) Field of Classification Search
USPC ......... 382/100, 103, 106, 128–134, 154, 168, 382/173, 181, 193, 199, 203, 209, 219, 232, 382/254, 274, 276, 286–292, 305, 312; 600/595; 703/11; 433/24, 58; 706/47
See application file for complete search history.

(56) References Cited

U.S. PATENT DOCUMENTS

| | | | |
|---|---|---|---|
| 5,160,262 A | 11/1992 | Alpern et al. | |
| 5,320,528 A * | 6/1994 | Alpern et al. | 433/58 |
| 8,070,487 B2 * | 12/2011 | Chishti et al. | 433/24 |
| 8,113,829 B2 * | 2/2012 | Sachdeva et al. | 433/24 |
| 8,382,686 B2 * | 2/2013 | Gutman et al. | 600/595 |
| 2002/0150859 A1 | 10/2002 | Imgrund et al. | |
| 2010/0145898 A1 * | 6/2010 | Malfliet et al. | 706/47 |
| 2011/0191081 A1 * | 8/2011 | Malfliet et al. | 703/11 |

FOREIGN PATENT DOCUMENTS

| | | |
|---|---|---|
| WO | 02/32340 A2 | 4/2002 |
| WO | 2008/131140 A2 | 10/2008 |
| WO | 2011/103876 A1 | 9/2011 |

OTHER PUBLICATIONS

PCT International Search Report and Written Opinion for PCT Application No. PCT/US2013/036602 mailed Sep. 16, 2013 (11 pages).

* cited by examiner

*Primary Examiner* — Seyed Azarian
(74) *Attorney, Agent, or Firm* — Sutherland Asbill & Brennan LLP

(57) ABSTRACT

Systems and methods for analyzing dynamic occlusion during replicated excursions of virtual three-dimensional representations of a dental patient's occlusal complex are provided. The method may include scanning a patient's jaws and teeth configuration using a medical imaging system such as CBCT, laser scanners, or traditional dental impressions; creating a virtual three-dimensional representation of the patient's occlusal complex; replicating excursions of the virtual three-dimensional representation of the patient's occlusal complex based at least on virtual inter-condylar angles and distances; determining acceptable occlusal contacts and/or malocclusions within the virtual three-dimensional representation of the patient's occlusal complex based at least in part on virtual dynamic occlusion during the replicated excursions, and determining at least one virtual dental appliance and/or orthodontic repositioning of one or more teeth based at least in part on the one or more acceptable occlusal contacts and/or malocclusions within the virtual three-dimensional representation of the patient's occlusal complex.

18 Claims, 7 Drawing Sheets

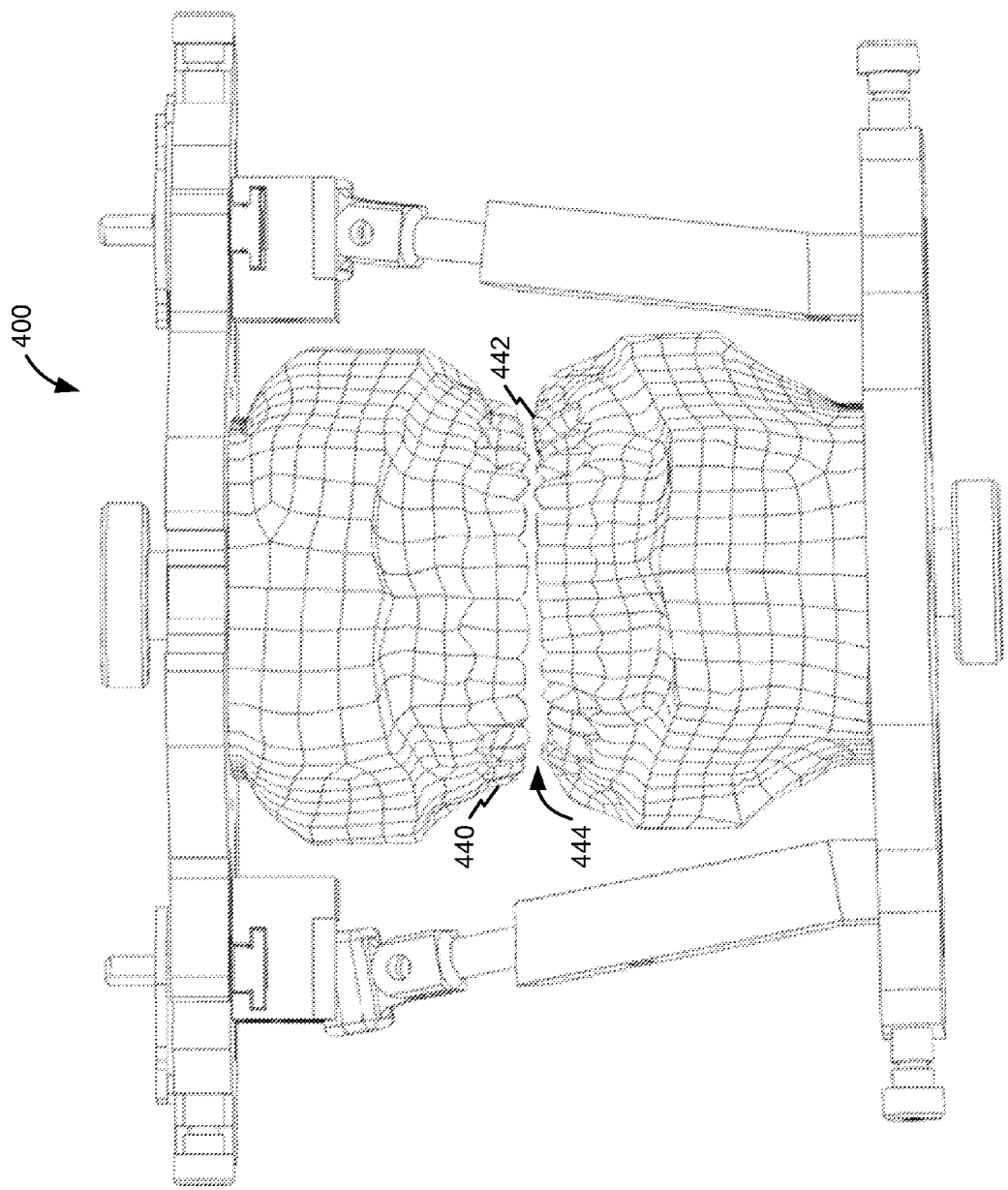

ary, dental implants, dentures, and/or other
SYSTEMS AND METHODS FOR ANALYZING DYNAMIC DENTAL OCCLUSIONS AND MAKING DENTAL APPLIANCES

BACKGROUND

The present disclosure relates generally to dentistry, and more particularly to systems and methods for analyzing dynamic dental occlusions for use in restorative dentistry, such as in the production of accurate replicas of a patient's teeth, for example, dental implants, dentures, and/or other appliances.

In order for a patient's teeth to function properly, the shape and position of every tooth must be in harmony with the opposing teeth. The maxillary teeth must be in harmony with the mandibular teeth so that the teeth can dynamically come together or occlude harmoniously. If upper and lower teeth do not fit properly when they move together, then abnormal, traumatic impacts of the teeth can occur. These traumatic impacts of teeth can cause pain and inflammation of the periodontal ligaments and bones which hold and support the teeth.

All mandibular and maxillary teeth have proprioceptive nerves which constantly send input to the brain. The proprioceptive nerves notify the brain of the functional contacts of the maxillary and mandibular teeth. If a malocclusion is present, some teeth will contact prematurely which places abnormal forces on these teeth. The affected teeth may send proprioceptive notices to the brain causing the brain to alter the muscles of mastication. These muscles react by altering jaw motion in an attempt to accommodate the offending occlusal contacts.

Altered muscle function can cause altered, abnormal forces on the fragile fibro-cartilage lining the temporomandibular joints (TMJ) and the fibro-cartilaginous discs. The potential result of these abnormal forces on the cartilage causes abnormal loading forces which cause excessive wear and potential degeneration. Human fibro-cartilage has no blood supply and thus no ability to heal. This cartilage either functions normally or abnormally wears and degenerates. Human fibro-cartilage also has no nerve supply and thus can not notify the brain that abnormal loading forces are causing this permanent damage. However, altered muscle function does cause abnormal loading forces on the TMJ capsule which does have nervous innervations. When TMJ capsular innovation is noted, additional altered muscular function can occur, potentially causing additional abnormal dental contacts and a vicious cycle of TMJ and dental degeneration and pathology results.

Typically, if a patient needs a dental appliance, such as a bridge or series of crowns, the teeth are prepared, and dental impressions (such as, for example, alginate or Poly Vinyl Siloxane (PVS) impressions) or digital laser scans are made. The impression and/or scan is sent to the dentist's laboratory where a CAD/CAM machine creates the dental appliance. However, the impression and/or scan does not create the proper occlusion or biting surface required for each patient. The impression and/or digital scan only creates a generic appliance which must be ground into occluding with the opposing teeth. This "tap, tap, grind" process can take hours. Moreover, the appliance fabricated in this manner does not consider dynamic occlusions. The impression and/or scan alone can not take into consideration the dynamic occlusions of the particular patient. Thus, the resulting finished product is a compromise and often can create further bite problems for the patients.

It therefore would be desirable to provide improved methods and systems for creating dental appliances, such as dental implants, dentures, and other fixtures.

SUMMARY

Some or all of the above needs and/or problems may be addressed by certain embodiments of the present application. Disclosed embodiments may include systems and methods for accurately analyzing dynamic occlusion during replicated excursions of a virtual three-dimensional representation of each patient's unique occlusal complex. In one aspect, a method is provided that includes scanning a patient's jaws and teeth using a medical imaging system, such as cone beam computed tomography (CBCT); creating a virtual three-dimensional representation of the patient's occlusal complex; replicating excursions of the virtual three-dimensional representation of the patient's occlusal complex based at least on virtual inter-condylar angles and distances; determining one or more acceptable occlusal contacts and/or malocclusions within the virtual three-dimensional representation of the patient's occlusal complex based at least in part on virtual dynamic occlusion during the replicated excursions, and determining at least one virtual dental appliance and/or orthodontic repositioning of one or more teeth based at least in part on the one or more acceptable occlusal contacts within the virtual three-dimensional representation of the patient's occlusal complex.

In other aspects, systems for carrying out such methods and for making dental appliances based on such virtual three-dimensional representations of the patient's occlusal complex are provided.

Other embodiments, aspects, and features of the invention will become apparent to those skilled in the art from the following detailed description, the accompanying drawings, and the appended claims.

BRIEF DESCRIPTION OF THE DRAWINGS

FIG. 7 is a schematic illustrating an interface according to yet another embodiment of the invention.

Figure 1:
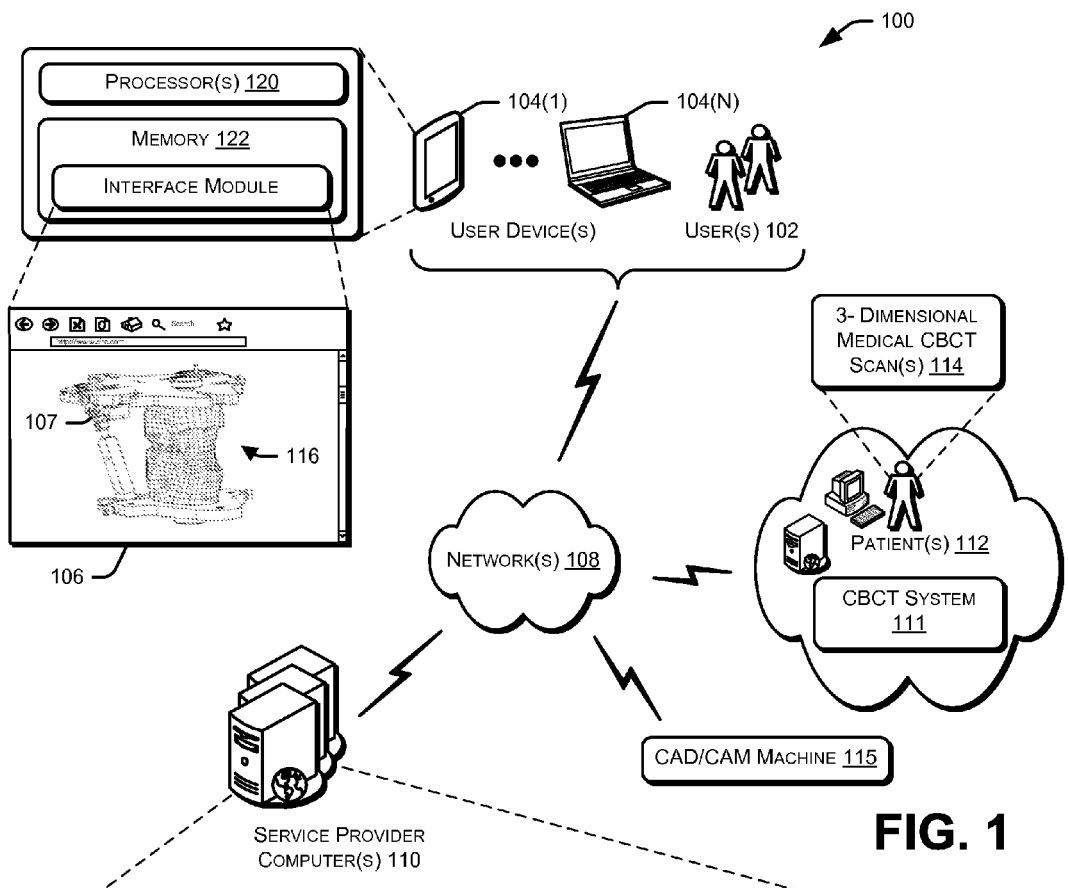
FIG. 1 is a schematic drawing of a system according to one embodiment of the invention.
Figure 1:
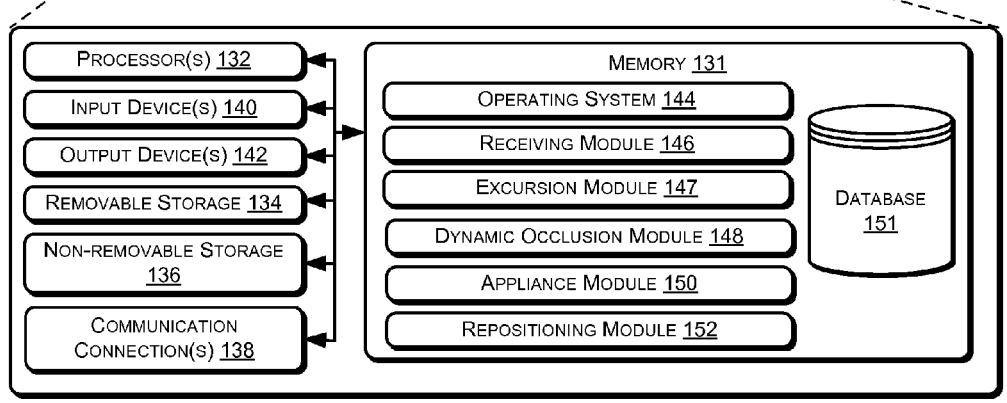

The appended drawing are not necessarily drawn to scale.

DETAILED DESCRIPTION

A virtual articulator has been developed, which can be set to accurately reflect an individual patient's unique tooth configurations, the inter-condylar angles and distances, and their relationship to the occlusal plane in three dimensions. This enables dental professionals to take an image (e.g., CBCT scan) of the patient's jaws and teeth, to analyze the image, re-create the patient's individualized anatomy and chewing motions in a virtual model, and then based on this information (e.g., digitally transmitted to a CAD/CAM machine) to construct dental appliances that will accurately fit and properly function in the patient's mouth.

The present systems and methods, unlike conventional approaches, can take a 3-D image from cone beam CT scans (or three 2D cephalometric x-rays) of a patient and enable construction of dental and orthodontic appliances that will be anatomically correct from the tempomandibular joints (TMJ) to the teeth. The system accurately reproduces not just one or two chewing attack paths, but all of the multiple attack paths based on skeletal analysis of each condyles' inter-condylar angles and distances. This is important because a major part of each patients jaw movements (multiple attack paths) is determined by the anatomy of each patient's right and left TMJ condyles. In this manner, the virtual articulator described herein is a human replicator that, properly programmed, can accurately replicate (digitally) all of the patient's chewing strokes. This can save a dentist many hours of chair side adjustments per week, and many hours of patient discomfort can be eliminated.

Illustrative embodiments will now be described more fully hereinafter with reference to the accompanying drawings, in which some, but not all embodiments are shown. The present application may be embodied in many different forms and should not be construed as limited to the embodiments set forth herein; rather, these embodiments are provided so that this disclosure will satisfy applicable legal requirements. Like numbers refer to like elements throughout.

Illustrative embodiments are directed to, among other things, systems and methods for replicating excursions (i.e., movement of the mandible relative to the maxilla) in a virtual three-dimensional representation of a patient's jaws and teeth configuration ("the virtual occlusal complex"). The virtual occlusal complex include a three-dimensional representation of a patient's tooth configurations (both individually and collectively), the TMJs, and the inter-condylar distances and angles and their three dimensional relationship to the occlusal plane. During the replicated excursions, dynamic occlusion (i.e., contact between teeth when the mandible is moving relative to the maxilla) may be analyzed. For example, certain illustrative embodiments may be directed to a method for determining at least one dental appliance that is within one or more acceptable interferences (i.e., tooth-to-tooth contacts) of the virtual occlusal complex based at least in part on virtual dynamic occlusion. In some instances, the information related to the at least one virtual dental appliance may be transmitted to a machining means where a physical dental appliance may be constructed.

In an example embodiment, the patient's jaws and teeth configuration, his or her actual occlusal complex, may be scanned using a medical imaging system to create the virtual occlusal complex. The dataset from the medical imaging system may then be transmitted to a computer environment where the virtual occlusal complex may be analyzed. Specifically, the virtual occlusal complex may replicate excursions, such as, but not limited to, chewing, speaking, yawning, grinding, clenching, swallowing, and/or any other accurate replication of the patient's multiple chewing pathways, etc. During the replicated excursions, one or more acceptable occlusal contacts may be determined based at least in part on dynamic occlusion of the virtual occlusal complex. In addition, during the replicated excursions, one or more non-acceptable occlusal contacts (i.e., malocclusions) may be determined based at least in part on dynamic occlusion of the virtual occlusal complex. In this manner, the malocclusions may be rectified or ameliorated.

In some instances, at least one virtual dental appliance may be determined based at least in part on the one or more acceptable occlusal contacts and/or malocclusions during the replicated excursions of the virtual occlusal complex. For example, the system may include a database or library of various dental appliances, including, e.g., various tooth sizes, shapes, and shades. In this manner, a dental appliance may be chosen from the database that complies with the one or more acceptable occlusal contacts during the replicated excursions of the virtual occlusal complex. In other aspects, a dental appliance may be chosen from the database that may not initially comply with the one or more acceptable occlusal contacts during the replicated excursions of the virtual occlusal complex. In this case, the dental appliance from the database may be altered as needed to comply with the one or more acceptable occlusal contacts during the replicated excursions of the virtual occlusal complex. After the dental appliance is determined, the dataset of the at least one virtual dental appliance may be transmitted to a machining means, such as a CAD/CAM machine, for creating a physical dental appliance that may fit into a patient's mouth and provide instant harmonious dynamic occlusion.

In other instances, orthodontic repositioning of one or more teeth may be determined. The orthodontic repositioning of the one or more teeth may be based at least in part on the one or more acceptable occlusal contacts of the virtual occlusal complex during the replicated excursions. For example, the virtual occlusal complex may replicate a number of excursions. During the replicated excursions of the virtual occlusal complex, one or more acceptable occlusal contacts, as well as one or more malocclusions, may be determined. The teeth causing the malocclusions may then be virtually repositioned or shaped so as to eliminate the malocclusions, thereby facilitating harmonious dynamic occlusion during repeat replicated excursions.

Accordingly, both the at least one dental appliance and the orthodontic repositioning of the one or more teeth may be based at least in part on dynamic occlusion during the replicated excursions of the virtual occlusal complex. In some instances, the at least one dental appliance and the orthodontic repositioning of the one or more teeth may be updated, modified, refined, and/or adjusted, and the replicated excursions of the virtual occlusal complex repeated until harmonious dynamic occlusion is achieved. For example, with regard to the dental appliance, the virtual occlusal complex may replicate a number of excursions. During the replicated excursions of the virtual occlusal complex, one or more acceptable occlusal contacts as well as one or more malocclusions may be determined. A virtual dental appliance may then be "inserted" into the virtual occlusal complex and an additional excursion may be replicated. During the replicated excursions of the virtual occlusal complex including the virtual dental appliance, one or more acceptable occlusal contacts as well as possibly one or more malocclusions may be determined. If the virtual dental appliance is within the one or more acceptable occlusal contacts and no malocclusions are present, the dataset of the virtual dental appliance may be sent to a CAD/CAM machine or other manufacturing system known in the art, such as, for example, steriolythic machines. Conversely, if malocclusions are still present, the virtual dental appliance may be adjusted to eliminate the malocclusion and further excursions may be replicated. This process may be repeated as many times as needed until no malocclusions are present during the replicated excursion of the virtual occlusal complex including the virtual dental appliance. A similar process may be implemented when repositioning one or more teeth in the virtual occlusal complex. That is, one or more teeth may be repositioned and one or more excursions may be replicated as necessary until no malocclusions are present in the virtual occlusal complex having one or more repositioned teeth.

It is a particular advantage of the presently disclosed systems and methods that the time-consuming and imperfect process of reworking a physical dental appliance to try to approximate suitable occlusions is avoided. Beneficially, this process can now be done virtually, so that the physical dental appliance, produced from the virtual model, provides immediate and harmonious dynamic occlusion.

FIG. 1 depicts an illustrative architecture 100 in which techniques for analyzing dynamic occlusion during replicated excursions of a virtual occlusal complex may be implemented. In architecture 100, one or more users 102 (e.g., dentists, dental assistants, dental technicians, etc.) may utilize computing devices 104(1) . . . 104(N) to access an interface (or website) 106 that may be provided by, created by, or otherwise associated with a service provider via one or more networks 108. In some instances, the computing devices (collectively 104) may be configured to present or otherwise display the interface 106 to the one or more users 102. The networks 108 may include any one or a combination of multiple different types of networks, such as cable networks, the Internet, wireless networks, and other private and/or public networks. While the illustrated example represents users 102 accessing the interface 106 over the networks 108, the described techniques may equally apply in instances where the users 102 interact with a service provider via a personal computer, a kiosk, or in any other manner. It is also noted that the described techniques may apply in other arrangements (e.g., set-top boxes, etc.), as well as in non-client/server arrangements (e.g., locally stored software applications, etc.).

In some aspects, the interface 106 may allow the users 102 to access, receive from, transmit to, or otherwise interact with the service provider via one or more service provider computers 110. In some examples, the interface 106 may also allow users to receive, from the service provider computers 110 over the networks 108, information associated with one or more three-dimensional medical scans 114 of a patient 112. For example, through the interface 106, the user 102 may interact with or manipulate the virtual occlusal complex 116. Additionally, through the interface 106, the user 102 may cause the virtual occlusal complex 116 to replicate excursions. Moreover, through the interface 106, the user 102 may determine, analyze, create, and/or manipulate at least one virtual dental appliance and/or the orthodontic repositioning of the one or more teeth based at least in part on dynamic occlusion during the replicated excursions of the virtual occlusal complex 116.

The user devices 104 may be any type of computing devices including, but not limited to, desktop personal computers (PCs), laptop PCs, mobile phones, smart phones, personal digital assistants (PDAs), tablet PCs, game consoles, set-top boxes, wearable computers, e-readers, web-enabled TVs, cloud-enabled devices and work stations, and the like. In some instances, and as illustrated, each user device 104 may be equipped with one or more processors 120 and memory 122 to store applications and data, such as the virtual occlusal complex 116 that may be displayed on the interface 106 and/or enable access to the service provider computers 110, or elsewhere.

The service provider computers 110 may be any type of computing device such as, but not limited to, mobile, desktop, and/or cloud computing devices, such as servers. In some examples, the service provider computers 110 may be in communication with the user devices 104 via the networks 108, or via other network connections. The service provider computers 110 may include one or more servers, perhaps arranged in a cluster, as a server farm, or as individual servers not associated with one another. These servers may be configured to host a website viewable via the interface 106 or any other Web browser accessible by a user 102 such as, but not limited to, one or more of the user devices 104. By way of example and not limitation, suitable computing devices may include personal computers (PCs), servers, server farms, data centers, or any other device capable of storing and executing all or part of the disclosed features.

Still referring to FIG. 1, in one illustrative configuration, the service provider computers 110 may comprise at least a memory 131 and one or more processing units (or processor(s)) 132. The processor(s) 132 may be implemented as appropriate in hardware, software, firmware, or combinations thereof. Software or firmware implementations of the processor(s) 132 may include computer-executable or machine-executable instructions written in any suitable programming language to perform the various functions described.

Memory 131 may store program instructions that are loadable and executable on the processor(s) 132, as well as data generated during the execution of these programs. Depending on the configuration and type of service provider computers 110, memory 131 may be volatile (such as random access memory (RAM)) and/or non-volatile (such as read-only memory (ROM), flash memory, etc.). The service provider computers 110 may also include additional removable storage 134 and/or non-removable storage 136 including, but not limited to, magnetic storage, optical disks, and/or tape storage. The disk drives and their associated computer-readable media may provide non-volatile storage of computer-readable instructions, data structures, program modules, and other data for the computing devices. In some implementations, the memory 131 may include multiple different types of memory, such as static random access memory (SRAM), dynamic random access memory (DRAM), or ROM.

Memory 131, removable storage 134, and non-removable storage 136 are all examples of computer-readable storage media. For example, computer-readable storage media may include volatile and non-volatile, removable and non-removable media implemented in any method or technology for storage of information such as computer-readable instructions, data structures, program modules, or other data. Additional types of computer storage media that may be present include, but are not limited to, programmable random access memory (PRAM), SRAM, DRAM, RAM, ROM, electrically erasable programmable read-only memory (EEPROM), flash memory or other memory technology, compact disc read-only memory (CD-ROM), digital versatile discs (DVD) or other optical storage, magnetic cassettes, magnetic tape, magnetic disk storage or other magnetic storage devices, or any other medium which can be used to store the desired information and which can be accessed by the server or other computing device. Combinations of any of the above should also be included within the scope of computer-readable media. Alternatively, computer-readable communication media may include computer-readable instructions, program modules, or other data transmitted within a data signal, such as a carrier wave, or other transmission.

The service provider computers 110 may also contain communication connection(s) 138 that allow the service provider computers 110 to communicate with a stored database, another computing device or server, user terminals, and/or other devices on a network. The service provider computers 110 may also include input device(s) 140, such as a keyboard, mouse, pen, voice input device, touch input device, etc., and output device(s) 142, such as a display, speakers, printer, etc.

Turning to the contents of the memory 131 in more detail, the memory 131 may include an operating system 144 and one or more application programs or services for implementing the features disclosed herein including a receiving module 146, an excursion module 147, a dynamic occlusion module 148, an appliance module 150, a repositioning module 152, and a database 151. The receiving module 146 may be configured to receive information related to the three-dimensional medical scan 114 of the patient's jaws and teeth configuration, his or her actual occlusal complex. For example, a patient's actual occlusal complex may be scanned using a medical imaging system 111 to create the virtual occlusal complex 116. In this manner, the virtual occlusal complex 116 may be an exact replica of the patient's actual occlusal complex. The virtual occlusal complex 116 may include part or all of the patient's tooth configuration (both individually and collectively), the mandible, the maxilla, the temporal bone, the TMJs, and the inter-condylar distances and angles and the three dimensional relationship to the occlusal plane. The dataset from the medical imaging system 111 may then be transmitted to the receiving module 146 via the network 108, where the virtual occlusal complex 116 may be analyzed.

In a preferred embodiment, the medical imaging system 111 includes a cone beam computed tomography (CBCT) system for taking CBCT scans of the patient's jaws and teeth configuration, the patient's occlusal complex. CBCT is advantageous because of the minimal radiation of a dental cone beam CT scan, which markedly restricts and focuses the x-ray exposure to primarily the upper and lower jaws and related teeth. CBCT scans may comprise rotating an X-ray source positioned about the patient along a helical or spiraled trajectory. The CBCT scanner's X-ray source may emit a conical or cone-shaped beam, which may be monitored by a flat-panel detector at discrete points, e.g., observation angles, along the helical trajectory. For instance, one projection of the conical beams attenuation may be captured by the flat-panel detector at each discrete observation angle, such that a sequence of CBCT projections, e.g., periodic snapshots of the conical X-ray beam's attenuation, may be generated along the CBCT scanner's helical trajectory. The resulting sequence of projections may be processed, e.g., using CBCT reconstruction algorithms, to construct a CBCT image of the patient's occlusal complex. CBCT is widely used in the dental field and is well-known in the art. In other instances, the medical imaging system 111 may include an oral laser scanner. Also well-known in the art, oral laser scanners may include tongue blade shaped scanners that are placed on the teeth to make an accurate digital image of the teeth. The medical imaging system 111 may include the CBCT system, the oral laser scanner, or a combination thereof. In a preferred embodiment, the medical imaging system comprises CBCT.

In other embodiments, the medical imaging system 111 may include conventional computed tomography, radiography, magnetic resonance imaging, ultrasound, and/or other known or future medical imaging systems in the art.

The receiving module 146 may be configured to receive information related to any known or future medical imaging system used in the dental and/or broader medical field.

The memory 131 may further include an excursion module 147. The excursion module 147 may be configured to simulate excursions of the virtual occlusal complex 116. Excursions may simulate such motions as chewing, speaking, yawning, grinding, clenching, swallowing, and/or any other accurate replicated replication of the patient's multiple chewing pathways, etc. For example, when replicating chewing, the excursion module may simulate a variety of chewing motions, including chewing motions associated with hard foods, soft foods, and/or liquids. Moreover, the excursion module 147 may be configured to account for factors such as chewing speed, teeth and jaw twisting, and/or occlusion impact forces, etc. One will appreciate that any number of factors known to affect excursion motions and dynamic occlusion may be replicated by the excursion module 147.

In certain embodiments, the excursion motions may be based, at least in part, on the anatomy of the left and right TMJ as guided by the complex interaction of tooth interferences and the arc of closure as determined by the inter-condylar angles and distances and their relationship to the occlusal plane in three dimensions in the virtual occlusal complex 116. For example, in certain aspects, if the virtual occlusal complex 116 indicates that a patient has one right or left condyle which has a high angulation and distance to the opposing condyle, the condyle which has a higher inter-condylar angle and distance may cause lateral condylar movement to be a more vertical drop when opening and a more vertical rise when closing during the replicated excursions of the virtual occlusal complex 116. This increased condylar vertical rise causes the mandibular teeth on the contra-lateral side to move faster with a twist during closing movements. Thus, these teeth will collide or impact the opposing upper teeth with increased impact speed and twisting, which may be replicated by the excursion module 147.

In some instances, finite element analysis and other modeling algorithms and programs may be used to simulate the excursions of the virtual occlusal complex 116. For example, as discussed in greater detail below with reference to FIGS. 4-6, the user interface 106 may depict replicating the excursions based at least in part on the left and right TMJs using a virtual polycentric hinge joint replicator 107. The virtual polycentric hinge joint replicator 107 may be programmed to include a range of motion and/or constraints similar to a physical apparatus. Accordingly, in certain aspects, the excursions may be delineated by at least the replicated left and right TMJs as programmed and/or "set" in the virtual polycentric hinge joint replicator 107.

The memory 131 may further include a virtual dynamic occlusion module 148. The virtual dynamic occlusion module 148 may be configured to detect contact between the teeth during the replicated excursions of the virtual occlusal complex 116. Moreover, the virtual dynamic occlusion module 148 may be configured to determine one or more acceptable occlusal contacts based at least in part on the detected contact between the teeth during the replicated excursions, i.e., virtual dynamic occlusion. For example, the virtual dynamic occlusion module 148 may detect one or more occlusal contacts between the teeth during the replicated excursions of the virtual occlusal complex 116 and determine whether the virtual occlusal contacts are within an acceptable predetermined limit to ensure harmonious jaw function or whether the virtual occlusal contacts are malocclusions.

The memory 131 may further include an appliance module 150. The appliance module 150 may be configured to determine at least one virtual dental appliance that is within the one or more acceptable occlusal contacts based at least in part on dynamic occlusion of the virtual occlusal complex 116 during replicated excursions. For example, the at least one virtual dental appliance may include a crown, a bridge, a bite plate, braces, a cap or veneer, a complete denture, a partial denture, a filling, a retainer, a dental implant, and/or any other known prosthesis. Moreover, in certain embodiments, the memory 131 may include a database 151 (or library). The database 151 may store information associated with one or more virtual dental appliances, including, e.g., various tooth sizes, shapes, and/or shades, etc. In this manner, a virtual dental appliance may be chosen from the database 151 that complies with the one or more acceptable occlusal contacts during the replicated excursions of the virtual occlusal complex 116. In other aspects, however, a virtual dental appliance may be chosen from the database 151 that may not initially comply with the one or more acceptable occlusal contacts during the replicated excursions of the virtual occlusal complex 116. In this case, the virtual dental appliance from the database 151 may be altered as needed to comply with the one or more acceptable occlusal contacts during the replicated excursions of the virtual occlusal complex 116. In other embodiments, the virtual dental appliances may be created, by the user 102, from scratch or determined using an algorithm.

In some instances, after the virtual dental appliance is determined, the dataset of the at least one virtual dental appliance may be transmitted to a machining means, such as a CAD/CAM machine 115, for creating a physical dental appliance that may fit into a patient's mouth and provide instant harmonious dynamic occlusion, i.e., preempt malocclusions. For example, the dataset may include a detailed list of dimensions defining the dental appliance. While the machining means 115 has been described as a CAD/CAM machine, one will appreciate that any machining means for creating a dental appliance may be used, including, but not limited to, a three-dimensional printer, a CNC machine, a casting system, and/or a molding system, etc.

The memory 131 may further include a repositioning module 152. The repositioning module 152 may be configured to determine virtual orthodontic repositioning of one or more teeth within the one or more acceptable occlusal contacts of the virtual occlusal complex 116. In some instances, the virtual occlusal complex 116 may replicate a number of excursions. During the replicated excursions of the virtual occlusal complex 116, one or more acceptable occlusal contacts, as well as one or more non-acceptable occlusal contacts (i.e., malocclusions), may be determined. The teeth causing the malocclusions may then be virtually repositioned so as to eliminate the malocclusions, thereby facilitating harmonious dynamic occlusion during following replicated excursions of the virtual occlusal complex 116. For example, upper and lower teeth which may have increased impact speeds and twisting may be virtually shaped or repositioned so that each tooth's cuspal inclinations (i.e., biting surfaces) can tolerate these increased impact forces. Some teeth have long, slender cusps and tight interdigitation. In this case, such teeth may not tolerate dental cusps with precise, steep inclinations. When subjected to these high-speed biting and chewing impacts, the upper and lower teeth can break, excessively wear, and/or cause inflammation of the surrounding tooth ligaments, bone, and/or gum tissue, etc. Conversely, teeth on the contra-lateral side of a TMJ condyle with a very low inter-condylar angle have condyles which do not drop very far in opening and, thus, do not have to move with as much speed as those with high inter-condylar angles. These teeth may dynamically occlude or interdigitate more slowly with slower impact speeds and forces. These teeth can be virtually shaped with a long, slender cusp-shaped anatomy and function without trauma. Accordingly, the correct dynamic tooth cuspal shape and tooth position can be virtually determined so that the upper and lower teeth are individualized correctly and have tooth position and shape in harmony with the patient's individually angulated TMJs.

Various instructions, methods, and techniques described herein may be considered in the general context of computer-executable instructions, such as program modules, executed by one or more computers or other devices. Generally, program modules include routines, programs, objects, components, data structures, etc., for performing particular tasks or implementing particular abstract data types. These program modules and the like may be executed as native code or may be downloaded and executed, such as in a virtual machine or other just-in-time compilation execution environment. Typically, the functionality of the program modules may be combined or distributed as desired in various embodiments. An implementation of these modules and techniques may be stored on some form of computer-readable storage media.

The architecture 100 shown in FIG. 1 is provided by way of example only. Numerous other operating environments, system architectures, and device configurations are possible. Accordingly, embodiments of the present disclosure should not be construed as being limited to any particular operating environment, system architecture, or device configuration.

Figure 2:
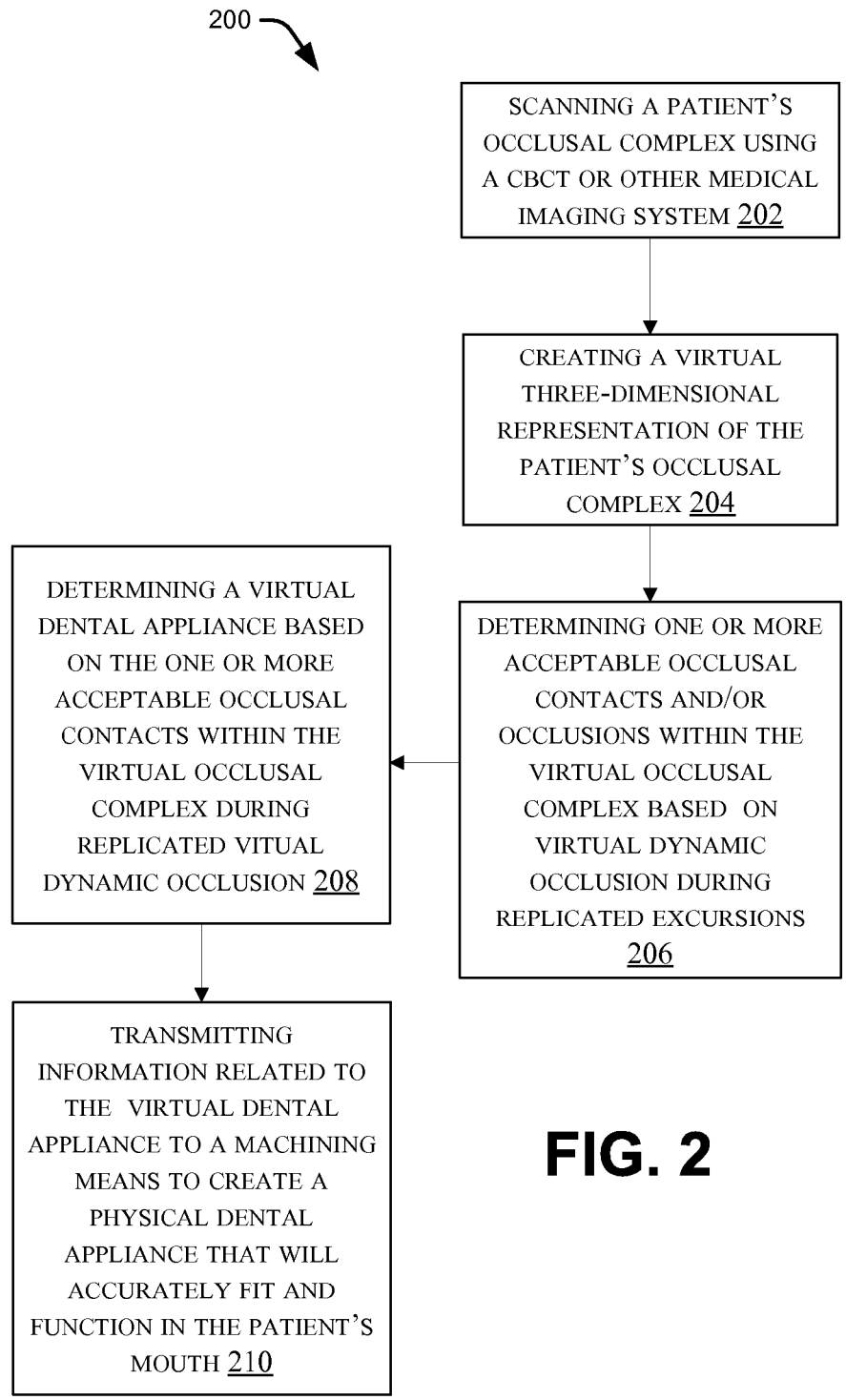
FIG. 2 is a process flow diagram illustrating a method according to one embodiment of the invention.
Figure 3:
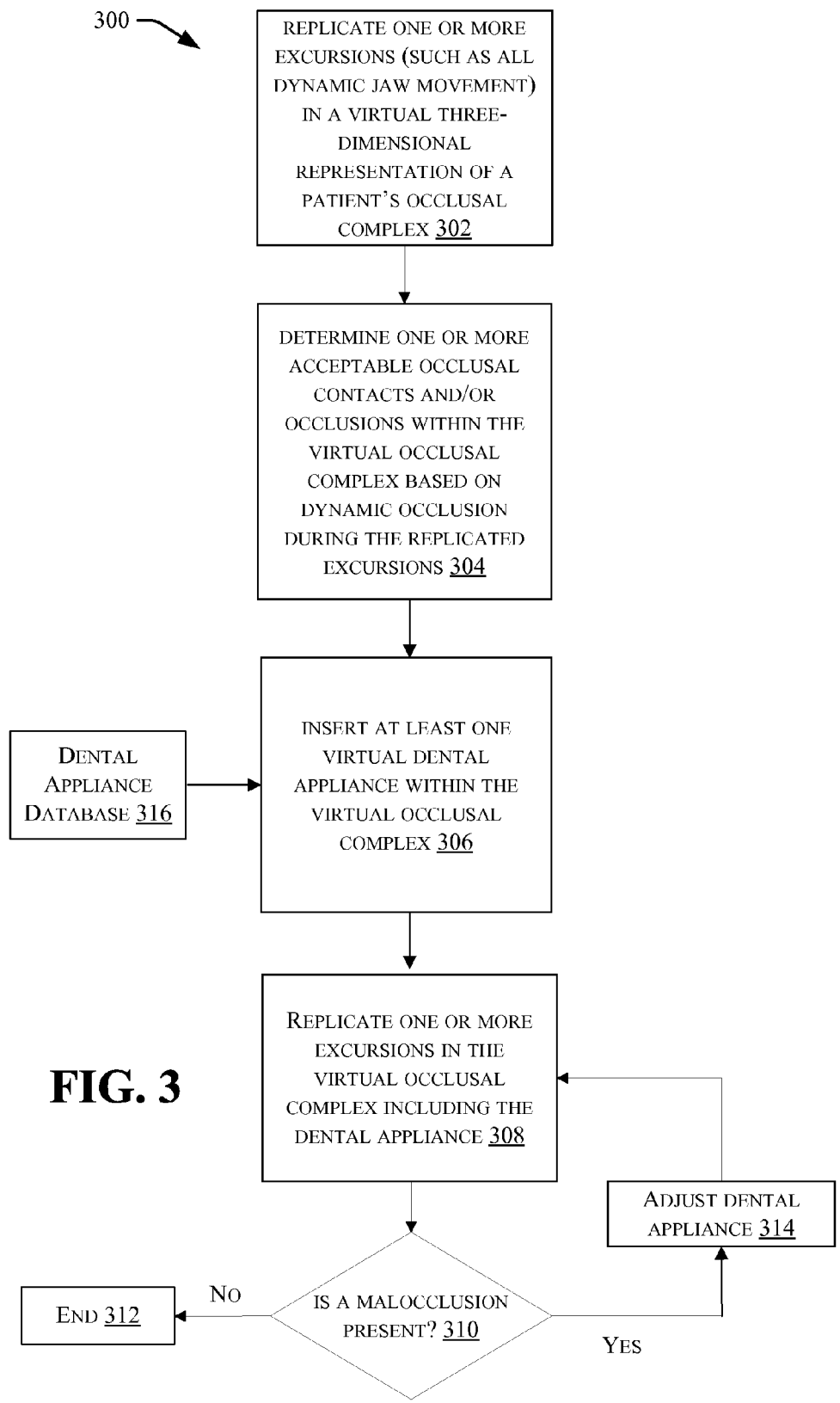
FIG. 3 is a flow diagram illustrating a method according to one embodiment of the invention.

FIGS. 2 and 3 illustrate example flow diagrams of methods for analyzing dynamic occlusion during replicated excursions of a virtual occlusal complex. In one example, the illustrative service provider computers 110 of FIG. 1 and/or locally stored software applications and/or one or more modules, alone or in combination, may perform the described operations of the methods. In one particular implementation, a method 200 may begin at block 202 of FIG. 2 in which the method 200 may include scanning a patient's jaws and teeth using a medical imaging system. For example, the medical imaging system may include a CBCT system and/or an oral laser scanner, and the patient's occlusal complex may include part or all of the teeth, the mandible, the maxilla, the temporal bone, the temporomandibular joint, and/or the inter-condylar distances and angles and their three dimensional relationship to the occlusal plane. Other known medical imaging systems may also be used. At block 204, the method 200 may include creating a virtual three-dimensional representation of the occlusal complex. For example, the scan of the patient's jaws and teeth configuration, or data therefrom, from block 202 may be transmitted over a network to a service provider or desktop software application where the scan is converted into a virtual three-dimensional representation of the patient's occlusal complex. In this manner, the virtual occlusal complex may be manipulated by a user, such as being made to replicate excursions, which may be dictated by virtual left and right TMJs of the patient as guided by the complex interaction of tooth interferences and the arc of closure as determined by the inter-condylar angles and distances and their relationship to the occlusal plane in three dimensions. At block 206, the method 200 may include determining one or more acceptable occlusal contacts and/or malocclusions within the virtual occlusal complex based at least in part on virtual dynamic occlusion during the replicated excursions. At block 208, the method 200 may include determining at least one virtual dental appliance based at least in part on the one or more acceptable occlusal contacts and/or malocclusion within the virtual occlusal complex during replicated dynamic occlusion. The virtual dental appliance may be chosen from a database or determined using an algorithm. At block 210, the method 300 may include transmitting information related to the at least one virtual dental appliance to a machining means to create a physical dental appliance that will accurately fit and function properly in a patient's mouth and provide instant harmonious dynamic occlusion. Similar methods as described in the method 200 may be used when virtually repositioning teeth.

In another particular implementation, a method 300 may begin at block 302 of FIG. 3 in which the method 300 may replicate one or more excursions (i.e., one or more dynamic jaw movements) in a virtual three-dimensional representation of a patient's occlusal complex. At block 304, the method 300 may include determining one or more acceptable occlusal contacts and/or malocclusions within the virtual occlusal complex based at least in part on virtual dynamic occlusion during the replicated excursions. At block 306, the method 300 may include inserting at least one virtual dental appliance into the virtual occlusal complex. In some aspects, the virtual dental appliance may be chosen from a database 316 of virtual dental appliances. At block 308, the method 300 may include replicating one or more excursions in the virtual occlusal complex. In this replicated excursions, however, the virtual occlusal complex includes the virtual dental appliance. At decision block 310, the method 300 may include determining whether a malocclusion is present during the replicated excursion of the virtual occlusal complex including the virtual dental appliance. If no malocclusion is present, the method may end at block 312. Conversely, at block 310, if a malocclusion is present, at block 314, then the virtual dental appliance may be adjusted. Such an adjustment may include changing the size or shape of a portion of the virtual dental appliance, or repositioning or reorienting of the dental appliance to relative to the patient's teeth. The virtual occlusal complex including the adjusted virtual dental appliance may then repeat block 308 until no malocclusions are present at block 310. Similar methods as described in the method 300 may be used when virtually repositioning teeth.

Illustrative systems and methods are described for analyzing virtual dynamic occlusion during replicated excursions of virtual occlusal complexes. Some or all of these systems and methods may, but need not, be implemented at least partially by architectures such as those shown in FIG. 1.

Figure 4:
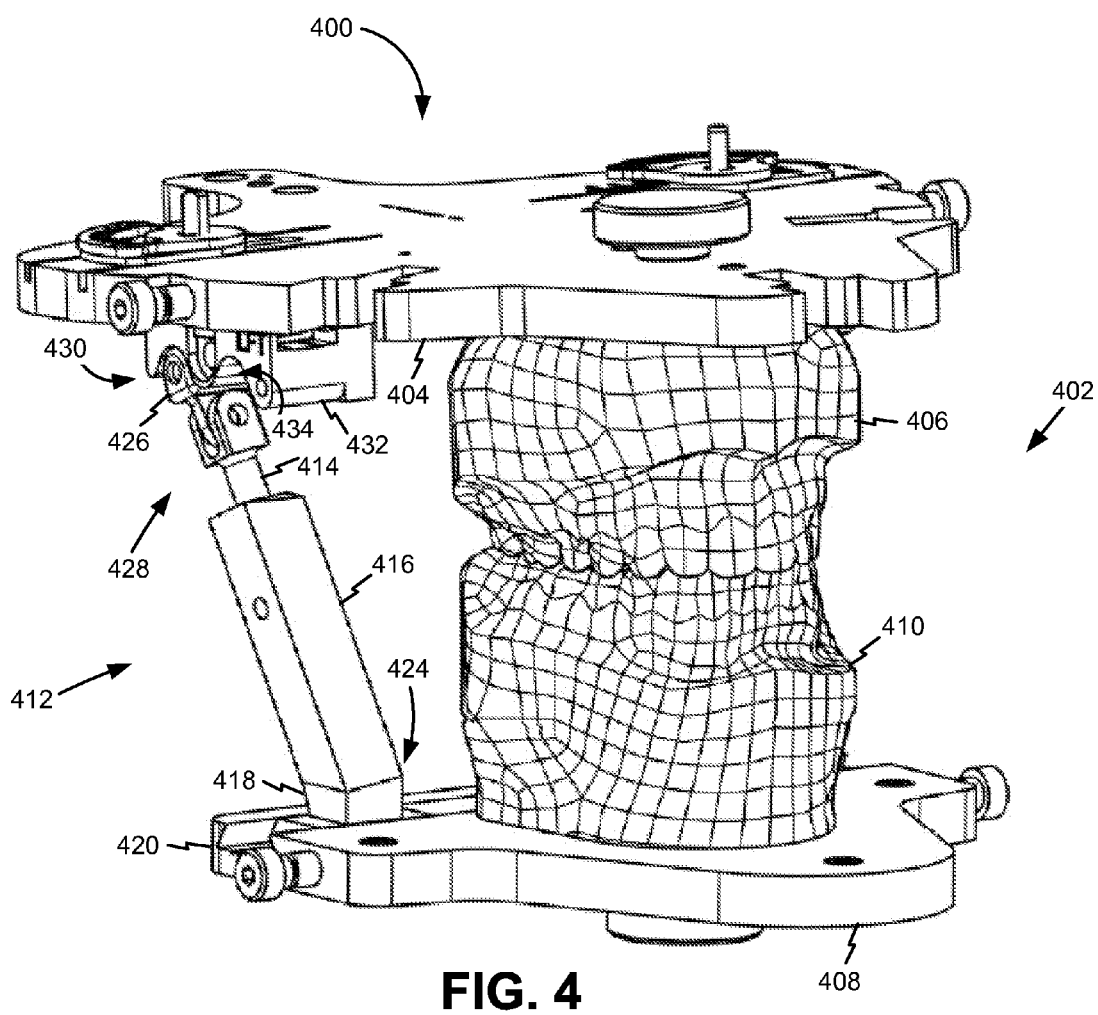
FIG. 4 is a schematic illustrating an interface according to one embodiment of the invention.
Figure 5:
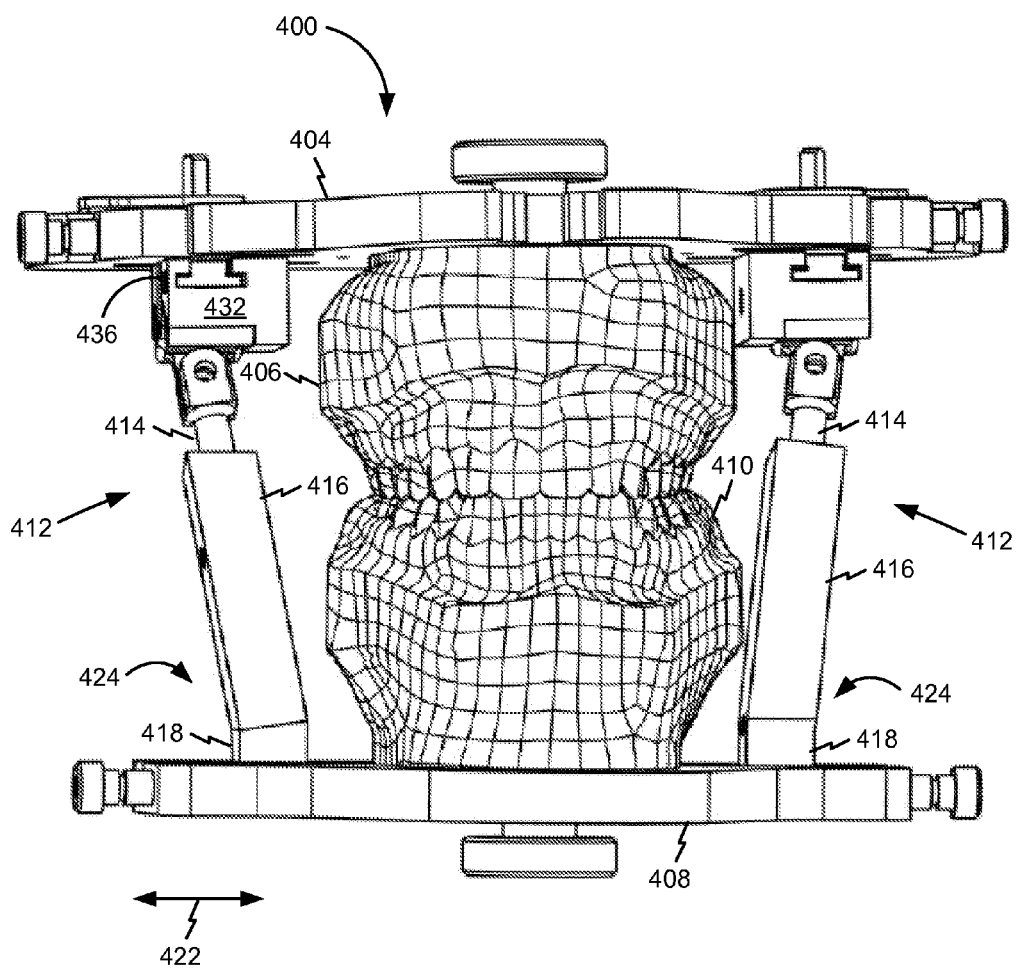
FIG. 5 is a schematic illustrating an interface according to another embodiment of the invention.
Figure 6:
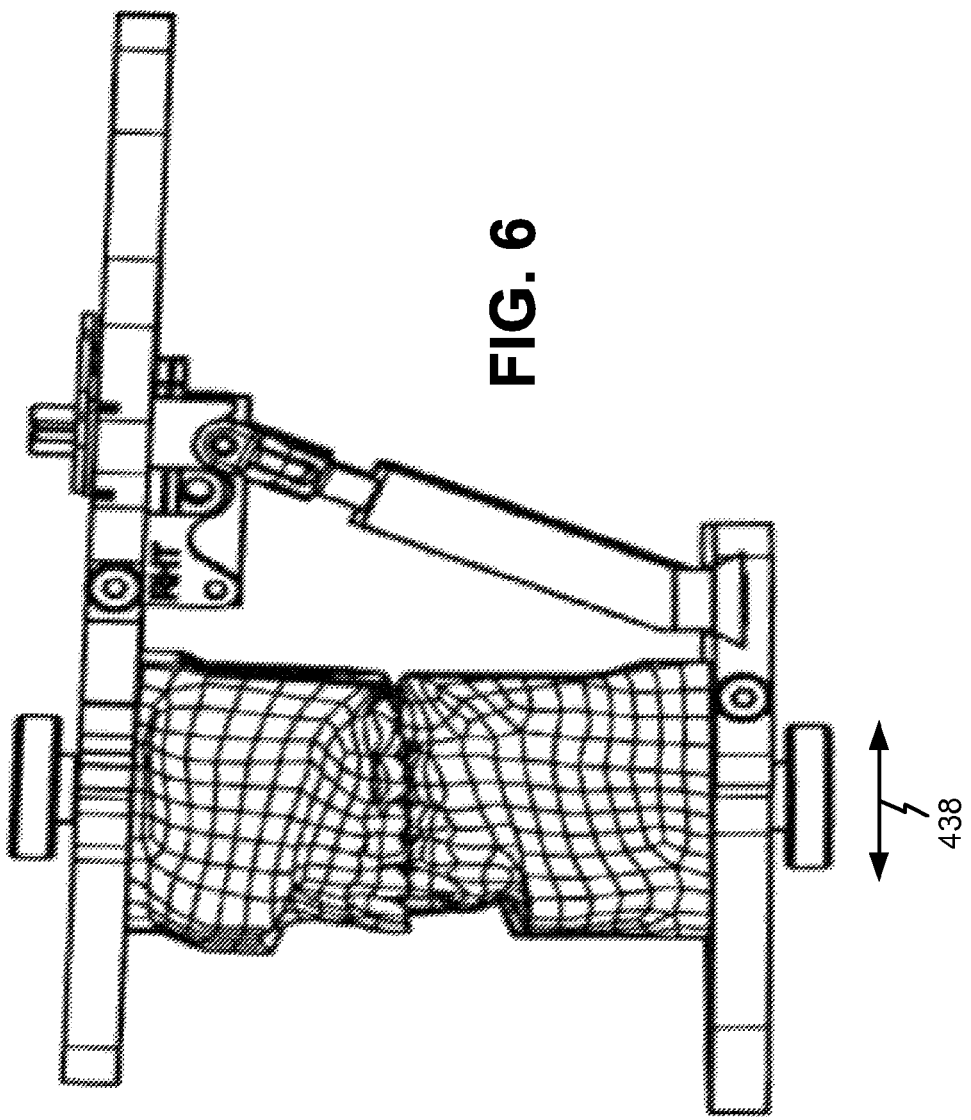
FIG. 6 is a schematic illustrating an interface according to yet another embodiment of the invention.

Illustrative embodiments of the application interface 106 in FIG. 1 may include a user interface as depicted in FIGS. 4-6. One will appreciate, however, that the user interface is simply a representation of finite elemental analysis algorithms, or other modeling systems, for replicating excursions of the virtual occlusal complex 116. Any number of user interfaces may be depicted, if depicted at all, or wholly omitted. The user interface merely depicts a visual representation of a device (e.g., virtual polycentric hinge joint replicator 107 in FIG. 1) that may replicate excursions.

In certain embodiments, the virtual articulator may be in communication with a physical polycentric hinge joint replicator, such as, but not limited to, those described in U.S. Pat. Nos. 5,160,262 and 5,320,528, which are both hereby incorporated by reference. In this manner, the virtual articulator may command one or more actuators associated with the physical polycentric hinge joint replicator so as to cause the physical polycentric hinge joint replicator to "chew." For example, the virtual articulator may be in communication with a number of servomotors associated with the physical polycentric hinge joint replicator. The virtual articulator may direct the servomotors to move the physical polycentric hinge joint replicator in a manner similar to the virtual replicator. Accordingly, the virtual replicator and the physical polycentric hinge joint replicator may replicate excursions of the patient's occlusal complex.

Turning now to FIGS. 4-6, in some embodiments, the user interface may depict a virtual polycentric hinge joint replicator 400. The replicator 400 may be depicted as including a similar structure and configuration as described in U.S. Pat. Nos. 5,160,262 and 5,320,528, which are both hereby incorporated by reference. For example, the user interface may depict the dental replicator 400 as supporting the virtual three-dimensional representation 402 of the patient's jaw and teeth configuration. In this manner, the dental articulator 400 may be depicted as including an upper support member 404 supporting a first virtual three-dimensional representation 406 of the patient's jaw and teeth configuration and a lower support member 408 supporting a second virtual three-dimensional representation 410 of a patient's jaw and teeth configuration. The lower support member 408 may be depicted as supporting a pair of axially spaced condyle support members 412. Each condyle support member 412 may be depicted as including a condyle 414, a central support section 416, and a lower mounting end 418. The lower mounting end 418 of each condyle support member may be depicted as being slidably mounted to the lower support member 408. That is, lower mounting end 418 may be depicted as capable of sliding within an axially extending slot 420.

The axially extending slot 420 may be depicted as including a dovetail cross-sectional shape designed to receive a corresponding mating configuration in the lower mounting end 418 of condyle support member 412 so as to prevent vertical movement therebetween. Therefore, the condyle support member 412 may be depicted as being able to freely slide in the axial direction indicated by arrows 422, allowing the two condyle support members 412 to be spaced axially apart a distance as desired by the user.

The angle of condyle support member 412 may be adjusted with respect to the lower support member 408. For example, the condyle support member 412 may be depicted as including a hinged portion 424 for adjusting the angle between the condyle support member 412 and the lower support member 408.

Each condyle 414 may be depicted as slidably (or telescopically) mounted to its associate central support section 416. Each condyle 414 may also be depicted as including an upper engaging section 426 and a hinged section 428 extending therefrom. For example, the hinged section 428 may be depicted as a mechanical linkage between the upper engaging section 426 and the condyle 414.

Upper engaging section 426 may be depicted as engaging a fossae recess 430 in a fossae block member 432 which is secured to upper support member 404. A forward capture recess 434 is provided in fossae block member 432 to capture and receive upper engaging section 426 in the event that engaging section 426 comes out of its associated fossae recess 430. The area between the fossae recess 430 and capture recess 434 replicates the superior eminence of the TMJ.

The fossae block members 432 are each depicted as being slidably mounted with respect to upper support member 404 such that the axial distance therebetween may be varied as desired. In addition, the fossae block members 432 are each depicted as being slidably mounted with respect to upper support member 404 such that the anterior-posterior distance may be varied as desired. For example, the fossae block members 432 may be depicted as including an inverted T-shaped slot 436 designed to receive a corresponding mating configuration extending from the upper support member 404. Therefore, the fossae block members 432 may be depicted as being able to freely slide in the anterior-posterior direction indicated by arrows 438.

Each fossae block member 432 and its associated condyle 414 may be depicted as cooperating so as to provide a polycentric hinge joint which replicates the TMJ of an individual.

In use, the first and second virtual three-dimensional representations 406 and 410 of the patient's jaw and teeth configuration are depicted as being mounted to the upper and lower support members 404 and 408, respectively. The lower support member 408 may be depicted as moving freely to replicate the excursions. Since the condyle 414 is not depicted as being permanently affixed to the fossae block member 432, the condyle 414 is depicted as being allowed to freely move within the fossae recess 430. The condyle 414 is depicted as being capable of moving downward and axially inward much in the same way the condyle of an actual jaw moves in a human being. The upper engaging section 426 moves in response to movement of the lower support member 408, and thus provides a replicated virtual polycentric hinge for the TMJ. The lower support member 408 can replicate movement in any direction permitted so as to replicate actual movement. Additionally, the condyle 414 moves such that it engages fossae recess 430, replicating a human TMJ, thus allowing the upper engaging section 426 to ride on the area of fossae block member 432, which replicates the superior eminence.

FIG. 7 depicts the virtual polycentric hinge joint replicator 400 in a mid-chewing motion, with the upper teeth 440 and lower teeth 442 slightly spaced apart. During the replicated chewing motions, however, the upper teeth 440 and lower teeth 442 may be moved to and/or positioned at various locations as dictated by the replicated tooth configurations, the replicated inter-condylar angles and distances, and their relationship to the occlusal plane in three dimensions. As discussed above, the virtual polycentric hinge joint replicator 400 may replicate any number of excursions or the like, such as, but not limited to, chewing, speaking, yawning, grinding, clenching, swallowing, and/or any other accurate replication of the patient's multiple chewing pathways, etc. For example, during replicated chewing motions, one or more acceptable occlusal contacts may be determined. That is, as the upper teeth 440 and lower teeth 442 of the virtual occlusal complex are moved during the various replicated chewing motions, the virtual articulator system may determine one or more acceptable occusal contacts about the interface 444 of the upper teeth 440 and lower teeth 442. In addition, during the various replicated chewing motions, one or more non-acceptable occlusal contacts (i.e., malocclusions) may be determined about the interface 444 of the upper teeth 440 and lower teeth 442. In some instances, the malocclusions may be rectified or ameliorated by the virtual repositioning of one or more of the upper teeth 440 and/or lower teeth 442. The process of replicating various chewing motions and determining acceptable and non-acceptable occlusal contacts may be repeated as necessary until the malocclusions are eliminated.

The present invention may be understood with reference to the following non-limiting examples.

Prophetic Example—Crown Replacement

A patient will be identified as being in need of a crown. A cone beam CT scan will then made of the patient's teeth and jaws. The intercondylar distances and angles and the occlusal plane orientation and position will then be verified. These distances and angles and the CBCT scan digital information are imported into a virtual articulator, such as the virtual polycentric hinge joint replicator described herein.

Then the virtual articulator with this information will be used to have the patient virtually "chew" in order to identify interferences acceptable to the patient without the crown, i.e., before treatment occlusion.

Next, a digital (virtual) crown will be inserted into the patient's virtual occlusal complex. Then, the virtual articulator with the original and added information will be used to have the patient virtually "chew" in order to identify unacceptable interferences (e.g., high spots) to the patient with the crown, i.e., after treatment occlusion. The identified unacceptable interferences will then be digitally removed.

Next, the virtual articulator with the revised information will be used to again have the patient virtually "chew," this time in order to confirm safe occlusion. When confirmed, the digital information will be transferred to a CAD/CAM or other manufacturing system to produce a physical crown having the specifications (e.g., dimensions, placement site) identified as providing acceptable occlusion in the virtual occlusal complex.

The physical crown will then be installed in the patient dental work consistent with the virtual placement. Other dental appliances, such as bridges and dentures, and the like, for other patients will be made using the same methods and systems described herein for a crown.

Although embodiments have been described in language specific to structural features and/or methodological acts, it is to be understood that the disclosure is not necessarily limited to the specific features or acts described. Rather, the specific features and acts are disclosed as illustrative forms of implementing the embodiments.

We claim:

1. A system comprising:
   at least one memory that stores computer-executable instructions; and
   at least one processor configured to access the at least one memory, wherein the at least one processor is configured to execute the computer-executable instructions to:
   receive at least one scan of a patient's jaws and teeth configuration from a medical imaging system;
   create a virtual three-dimensional representation of the patient's occlusal complex based at least in part on the at least one scan from the medical imaging system;
   replicate excursions of the virtual three-dimensional representation of the patient's occlusal complex;
   determine one or more acceptable occlusal contacts within the virtual three-dimensional representation of the patient's occlusal complex based at least in part on virtual dynamic occlusion;
   determine at least one virtual dental appliance based at least in part on the one or more acceptable occlusal contacts within the virtual three-dimensional representation of the patient's occlusal complex; and
   transmit information related to the at least one virtual dental appliance to a CAD/CAM machine to create a physical dental appliance having dimensions corresponding to the virtual dental appliance, wherein replicating excursions of the virtual three-dimensional representation of the patient's occlusal complex is based at least in part on a virtual polycentric hinge joint replicator.

2. The system of claim 1, wherein the medical imaging system comprises cone beam computed tomography.

3. The system of claim 1, wherein replicating excursions of the virtual three-dimensional representation of the patient's occlusal complex is based at least in part on a virtual left and right temporomandibular joint as guided by virtual interactions of virtual tooth interferences and a virtual arc of closure as determined by virtual inter-condylar angles and distances and their relationship to a virtual occlusal plane in three dimensions.

4. The system of claim 1, wherein the physical dental appliance is selected from crowns, bridges, bite plates, braces, caps, complete dentures, partial dentures, veneers, fillings, retainers, dental implants, and combinations thereof.

5. The system of claim 1, wherein the at least one processor is further configured to execute the computer-executable instructions to determine virtual orthodontic repositioning of one or more teeth based at least in part on the one or more acceptable occlusal contacts within the virtual three-dimensional representation of the patient's occlusal complex.

6. The system of claim 1, wherein replicating excursions of the virtual three-dimensional representation of the patient's occlusal complex is based at least in part on one or more of the following: chewing, speaking, yawning, swallowing, or a replicated chewing pathway.

7. The system of claim 1, wherein the at least one processor is further configured to execute the computer-executable instructions to communicate with one or more actuators associated with a physical polycentric hinge joint replicator so as to cause the physical polycentric hinge joint replicator to replicate excursions of the patient's occlusal complex.

8. A method comprising:
   scanning a patient's jaws and teeth configuration using a medical imaging system;
   creating a virtual three-dimensional representation of the patient's occlusal complex based on said scanning;
   replicating excursions of the virtual three-dimensional representation of the patient's occlusal complex;
   determining one or more acceptable occlusal contacts within the virtual three-dimensional representation of the patient's occlusal complex based at least in part on dynamic occlusion during the replicated excursions;
   determining orthodontic repositioning of one or more teeth based at least in part on the one or more acceptable occlusal contacts within the virtual three-dimensional representation of the patient's occlusal complex;
   determine at least one virtual dental appliance based at least in part on the one or more acceptable occlusal contacts within the virtual three-dimensional representation of the patient's occlusal complex; and
   transmitting information related to the at least one virtual dental appliance to a CAD/CAM machine to create a physical dental appliance having dimensions corresponding to the virtual dental appliance.

9. The method of claim 8, wherein the physical dental appliance is selected from crowns, bridges, bite plates, braces, caps, complete dentures, partial dentures, veneers, fillings, retainers, dental implants, and combinations thereof.

10. The method of claim 8, wherein replicating excursions of the virtual three-dimensional representation of the patient's jaw and teeth configuration comprises one or more of the following: chewing, speaking, yawning, grinding, clenching, swallowing, or a replicated chewing pathway.

11. The method of claim 8, wherein the medical imaging system comprises cone beam computed tomography (CBCT).

12. A method comprising:
   (a) replicating an excursion in a virtual three-dimensional representation of a patient's occlusal complex;
   (b) determining one or more acceptable occlusal contacts and occlusions within the virtual three-dimensional representation of the patient's occlusal complex based at least in part on virtual dynamic occlusion during the replicated excursions;
   (c) inserting at least one virtual dental appliance into the virtual three-dimensional representation of the patient's occlusal complex;
   (d) replicating an excursion in the virtual three-dimensional representation of the patient's occlusal complex including the at least one virtual dental appliance;
   (e) determining whether a malocclusion is present during the replicated excursion of the virtual three-dimensional representation of the patient's occlusal complex including the at least one virtual dental appliance;
   (f) if a malocclusion is present, adjusting the at least one virtual dental appliance;
   (g) repeating steps (d) through (f) until no malocclusion is present; and
   (h) transmitting information related to the at least one virtual dental appliance to a CAD/CAM machine to create at least one physical dental appliance having dimensions corresponding to the at least one virtual dental appliance presenting no malocclusions during the replicated excursion of the virtual three-dimensional representation of the patient's occlusal complex.

13. The method of claim 12, wherein the virtual three-dimensional representation of the patient's occlusal complex is produced from a cone beam computed tomography (CBCT) scan of the patient's jaws and teeth.

14. The method of claim 12, wherein the replicating of an excursion in the virtual three-dimensional representation of the patient's occlusal complex comprises one or more of the following: chewing, speaking, yawning, grinding, clenching, swallowing, or a replicated chewing pathway.

15. The method of claim 12, further comprising determining orthodontic repositioning of one or more teeth based at least in part on the one or more acceptable occlusal contacts within the virtual three-dimensional representation of the patient's occlusal complex.

16. A method, comprising:
   (a) replicating an excursion in a virtual three-dimensional representation of a patient's occlusal complex;
   (b) determining one or more acceptable occlusal contacts and malocclusions within the virtual three-dimensional representation of the patient's occlusal complex based at least in part on virtual dynamic occlusion during the replicated excursions;
   (c) repositioning of one or more of the patient's teeth based at least in part on the one or more acceptable occlusal contacts within the virtual three-dimensional representation of the patient's occlusal complex;
   (d) replicating an excursion in the repositioned virtual three-dimensional representation of the patient's occlusal complex;
   (e) determining whether a malocclusion is present during the replicated excursion of the repositioned virtual three-dimensional representation of the patient's occlusal complex including the at least one dental appliance;
   (f) if a malocclusion is present, virtually repositioning one or more of the patient's teeth;
   (g) repeating steps (d) through (f) until no malocclusion is present;
   (h) determining at least one virtual dental appliance based at least in part on the one or more acceptable occlusal contacts within the virtual three-dimensional representation of the patient's occlusal complex; and
   (i) transmitting information related to the at least one virtual dental appliance to a CAD/CAM machine to create at least one physical dental appliance having dimensions corresponding to the at least one virtual dental appliance presenting no malocclusions during the replicated excursion of the virtual three-dimensional representation of the patient's occlusal complex.

17. The method of claim 16, wherein replicating excursions of the virtual three-dimensional representation of the patient's occlusal complex comprises one or more of the following: chewing, speaking, yawning, swallowing, or a replicated chewing pathway.

18. The method of claim 16, wherein the virtual three-dimensional representation of the patient's occlusal complex is produced from a cone beam computed tomography (CBCT) scan of the patient's jaws and teeth.

* * * * *